United States Patent [19]

Smid

[11] 4,216,156
[45] Aug. 5, 1980

[54] STABLE CONCENTRATED SOLUTION OF GLYCIDYLTRIMETHYLAMMONIUM CHLORIDE AND PROCESS FOR PREPARING STABLE CONCENTRATED SOLUTIONS OF GLYCIDYLTRIMETHYLAMMONIUM CHLORIDE

[75] Inventor: Jacob K. Smid, Bodegraven, Netherlands

[73] Assignee: Chem-Y, Fabriek van Chemische Produkten, B.V., Bodegraven, Netherlands

[21] Appl. No.: 5,589

[22] Filed: Jan. 22, 1979

[30] Foreign Application Priority Data

Jan. 27, 1978 [NL] Netherlands ..................... 7801007

[51] Int. Cl.$^2$ ................ C07D 301/34; C07D 303/36
[52] U.S. Cl. ........................ 260/348.38; 260/348.44
[58] Field of Search ..................... 260/348.38, 348.44

[56] References Cited

U.S. PATENT DOCUMENTS

| | | | |
|---|---|---|---|
| 2,876,217 | 3/1959 | Paschall | 260/348.44 |
| 3,342,840 | 9/1967 | Sobolev | 260/348.44 |
| 4,066,673 | 1/1978 | Doughty et al. | 260/348.44 |

FOREIGN PATENT DOCUMENTS

| | | | |
|---|---|---|---|
| 2303886 | 8/1973 | Fed. Rep. of Germany | 260/348.44 |
| 1056587 | 1/1967 | United Kingdom | 260/348.44 |
| 1140520 | 1/1969 | United Kingdom | 260/348.44 |
| 1335760 | 10/1973 | United Kingdom | 260/348.44 |
| 1352205 | 5/1974 | United Kingdom | 260/348.44 |

OTHER PUBLICATIONS

James D. McClure, J. Org. Chem., vol. 35, No. 6, 1970, pp. 2059–2061.
Derwent Abstract of Dutch Patent Application 66, 12576 in Netherlands Patents Report, vol. 5, No. 10 (5:General Organic p.1).
Derwent Abstract of Dutch Patent Application 7612362, Accession No. 19376Y/11.

*Primary Examiner*—Norma S. Milestone
*Attorney, Agent, or Firm*—Browdy and Neimark

[57] ABSTRACT

Stable concentrated aqueous solutions of glycidyltrimethylammonium chloride are provided which contain the monohydrate of glycidyltrimethylammonium chloride in a concentration of 90% to saturation, said solutions after dilution with water to a content of 25% glycidyltrimethylammonium chloride showing a pH of less than 12.5. Furthermore a process is provided for preparing stable concentrated solutions of glycidyltrimethylammonium chloride, wherein anhydrous glycidyltrimethylammonium chloride is mixed with an excess of water over the amount necessary for forming the desired solution, whereafter the excess of water is evaporated under reduced pressure. Also the invention provides the monohydrate of glycidyltrimethylammonium chloride as a novel substance.

5 Claims, No Drawings

STABLE CONCENTRATED SOLUTION OF GLYCIDYLTRIMETHYLAMMONIUM CHLORIDE AND PROCESS FOR PREPARING STABLE CONCENTRATED SOLUTIONS OF GLYCIDYLTRIMETHYLAMMONIUM CHLORIDE

Glycidyltrimethylammonium chloride is an important chemical, e.g. for the starch industry and for the preparation of cationic surfactants. In Example 4 of U.S. Pat. No. 2,876,217 its preparation from trimethylamine and epichlorohydrin is disclosed in an aqueous medium. According to an article by McClure in J. Org. Chem. 35, 2059–2061 (1970) only a low yield is obtained in this process, and also the obtained product on standing at 25° C. decomposes so quickly that already after one week no significant epoxide content is found any more. This has been confirmed by experiments carried out by the present Applicant, wherein it appeared furthermore that the solution obtained according to Example 4 of U.S. Pat. No. 2,876,217 before the concentration had already a pH of 12.9.

In the abovementioned article by McClure it is proposed to carry out the preparation of the glycidyltrimethylammonium chloride in an organic solvent and as such a solvent preferably an excess of the epichlorohydrin is used. It is stated generally that the synthesis can best be carried out in a solvent, wherein the product possesses a low solubility, and the low yield in the synthesis of this product in water is ascribed to the high solubility of the glycidyltrimethylammonium chloride in water, due to which it remains available for further reactions.

The above-discussed article by McClure is representative for the understandings about glycidyltrimethylammonium chloride which existed up till now. Thus, the Dutch patent application No. 6514023 proposes to carry out the synthesis of this compound in an anhydrous medium, and as such various kinds of organic solvents are mentioned. On page 2, of German Offenlegungsschrift No. 2,055,046 the difficulty is discussed to remove unreacted epichlorohydrin from the product. It is mentioned there that this can only be carried out under very mild reaction conditions, for example by distilling several times with water vapor under strongly reduced pressure at 30° C., which of course is particularly disagreeable for a technical process and wherein one should still reckon with a hydrolysis of the product up to 20%. This also is an important aspect of the problems which play a role with this product, since for use in the starch industry the glycidyltrimethylammonium chloride should possess a content of free epichlorohydrin of less than 70 parts pro million (vide German Offenlegungsschrift No. 2,056,002). Furthermore, according to page 2 of German Offenlegungsschrift No. 2,303,886, it is impossible to sell compounds of this kind in the form of aqueous solutions, because they have the tendency to hydrolyze in water.

A different opinion is found in Dutch patent application No. 6516333. According to this patent application the solid glycidyltrimethylammonium chloride would be instable at moderate temperatures, whereas on the contrary aqueous solutions having a content of 70–80% glycidyltrimethylammonium chloride would be stable. The application contains the explicit warning that the concentration of the solution should not be too high, because at a concentration of over 80% by weight the solution would become solid at temperatures, to which it would be subjected during storage, transportation and handling.

The statements in patent application No. 6516333 are contrary to what has been observed by Applicant. Thus, it was established that solid glycidyltrimethylammonium chloride is more stable than a solution thereof having a concentration up to 80% by weight. Furthermore, it appears that the data of the abovementioned application point to a decomposition of 5% per month at the highest concentration (76.9 % of epoxide) actually investigated in patent application No. 6516333, which is not acceptable for a commercial product, because due to this storage during a reasonable time is impossible, which, according to the experience of Applicant, is not true for the anhydrous solid glycidyltrimethylammonium chloride. Finally, it is neither correct that solutions having a concentration of more than 80% by weight easily solidify at normal temperatures of transportation and storage, as will appear hereinafter from the experimental part.

In practice the teachings of patent application No. 6516333 have not found acceptance, because up till now glycidyltrimethylammonium chloride always has been put onto the market in powdery form, also by the Applicant of patent application No. 6516333. However, this powder is strongly hygroscopic and has a tendency to dusting, and also the skin of some persons is oversensitive to this product. This means that the reconstitution with water by the user necessitates certain precautions.

In Dutch patent application No. 7612362, a divisional of patent application No. 6612576 in the name of the same applicant as above, these teachings are also not followed. That patent application describes the conversion of a glycidyltrialkylammonium halide with acrylic acid or a α-alkylacrylic acid, wherein the glycidyltrialkylammonium halide is used in aqueous solution. However, it does not appear from this application that the glycidyltrimethylammonium chloride would be stored in aqueous solution during any appreciable time. It is mentioned on page 3, lines 15–17 that the concentration of the glycidyltrialkylammonium halide in the aqueous solution can vary from 20 to 90% by weight and preferably from 50 to 80% by weight. In the actual examples of the application the work was done with three concentrations of glycidyltrimethylammonium chloride, i.e. with 69.5% by weight in Example I, 69% by weight in Example II and 71.4% by weight in Example III.

Accordingly, it is an object of the invention to provide stable concentrated aqueous solutions of glycidyltrimethylammonium chloride.

It is a further object to provide such stable aqueous solutions of glycidyltrimethylammonium chloride which contain less than 70 ppm epichlorohydrin, based on the anhydrous glycidyltrimethylammonium chloride.

A still further object is to provide a method of preparation of stable concentrated aqueous solutions of glycidyltrimethylammonium chloride which at the same time removes an undesirable excess of epichlorohydrin.

Another object of the invention is to provide the novel monohydrate of glycidyltrimethylammonium chloride.

Further objects and advantages will appear from the following description.

It has now been found that glycidyltrimethylammonium chloride forms a monohydrate and that this monohydrate in highly concentrated aqueous solution is substantially as stable as the glycidyltrimethylammonium chloride itself so that it can be marketed in this form.

As mentioned already, such a stable product is not obtained by working according to U.S. Pat. No. 2,876,217, but when the glycidyltrimethylammonium chloride is prepared in a non-aqueous medium, an aqueous solution of this product having the same concentration (25%) as is obtained as direct reaction product according to Example 4 of U.S. Pat. No. 2,876,217, possesses a pH of less than 12.5

Accordingly, this invention provides a stable concentrated aqueous solution of glycidyltrimethylammonium chloride, which is characterized by the fact that said solution contains the monohydrate of glycidyltrimethylammonium chloride in a concentration of 90% up to saturation, and after diluting with water to a glycidyltrimethylammonium chloride content of 25% shows a pH of less than 12.5

The glycidyltrimethylammonium chloride will be abbreviated hereinafter as "GTA".

It should be remarked here that under normal conditions saturated solutions of the monohydrate also comprise supersaturated solutions. It has been established experimentally that at ambient temperature (20° C.) an 85.4% aqueous solution of GTA can be considered a saturated solution of the monohydrate in the sense that crystallization thereof can be induced at refrigerator temperature with the aid of seeding crystals of the monohydrate. However, a solution of this concentration has been stored in a refrigerator (where accordingly it should become supersaturated) for several months without any crystallization occurring, and—which is even more surprising—crystallization neither occurred under these conditions, when small pieces of porcelain or the like, which, as is well-known, often act as crystallization nuclei, were added. In actual practice a GTA solution having a concentration of 85 to 86% is now preferred as commercial product.

The monohydrate of GTA can be prepared simply by mixing solid, anhydrous GTA with a small amount of water. It is possible to use exactly the amount of water required for forming the monohydrate, but this is not very practical, because in that case lumps are easily formed, and accordingly it is simpler to use an excess of water. This excess only needs to be small, because an extremely concentrated solution of the monohydrate is already a liquid having a not too high viscosity. The monohydrate itself is a crystalline solid having a melting point of 42°–44° C., which as simple calculation teaches, contains 10.6% of water. A solution having a total water content of 15%, i.e. a mixture of more than 95% of the monohydrate of GTA with less than 5% of free water is already a well manageable liquid for which at 20° C. a viscosity of about 400 cp was found. For working on a technical scale, however, this process is less suitable, because the dissolving of the anhydrous GTA in such amounts of water requires much time and an intensive mixing.

A technically more suitable possibility is to add more water to the anhydrous GTA than should be present in the final concentrated solution, and then evaporate this excess again from the mixture at a low pressure and temperature. This last mentioned embodiment has a further advantage, if one starts from an anhydrous GTA which contains a higher content of residual epichlorohydrin than is permissible for the final use, for epichlorohydrin and water from an azeotrope which boils at 88° C. under atmospheric pressure. Thus, this invention also provides a particularly simple process for liberating GTA of an undesirable excess of epichlorohydrin. To this end the anhydrous GTA can be simply dissolved in water in a concentration of for example 50% (generally about 20–70%), and this solution can then be evaporated at a low pressure (generally less than 15 kPa) and a corresponding low temperature until the water content has decreased so far as corresponds to the desired concentration, for example at least 90% of the GTA monohydrate. However, if lower concentrations are permissible, because the product has not to be stored for a long time, also solutions of lower concentrations can be prepared in this way, which still has the advantage that an undesirable excess of epichlorohydrin is removed azeotropically. With this simple evaporation the difficulties mentioned on page 2 of German Offenlegungsschrift No. 2,055,046 are not experienced. Due to this not only the stable concentrated solution of the GTA monohydrate is obtained, but also the undesirable epichlorohydrin is removed to such an extent that it will still only be present in an amount of some tens parts per million.

The following experimental data will elucidate the invention further.

1. PREPARATION OF THE MONOHYDRATE OF GTA

A saturated solution of GTA in water was prepared (85.4%). Seeding crystals for this solution were obtained by slightly moistening anhydrous GTA. Thereby a hard crust is formed on the particles and it has appeared that this crust is the monohydrate. The saturated solution was seeded with this material and then kept in a refrigerator overnight. Needle-like crystals were obtained and these were washed with ether and dried under reduced pressure. It appeared that the water content of the product was about 10.6%, which corresponds to the expected value for the monohydrate. The melting point was 42°–44° C.

2. STABILITY EXPERIMENTS a. Anhydrous powdery GTA

Anhydrous powdery GTA was stored in a closed container at 20° C. In the course of 9 months the epoxide content decreased from 6.43 meq/g (97%) to 5.99 meq/g (91%), i.e. a decrease of 6% in 9 months. This is less than the decrease of 5% in one month at 25° C. mentioned in the left column of page 2060 of the article by McClure. It is not known whether causes other than the 5 K temperature difference play a role therein.

b. GTA hydrate

On Aug. 17, 1977 it was established that a GTA hydrate had an epoxide content of 5.57 meq/g (94.4% of the theoretical value). On Nov. 16, 1977 it appeared that the epoxide content was still 5.51 meq/g (93.4%) and on Jan. 2, 1978 it was still 5.45 meq/g (92.4%). Also this experiment was carried out at 20° C.

c. Solution of 91.7% GTA hydrate (82% anhydrous GTA and 18% water)

Also this experiment was carried out at 20° C. The following epoxide values were obtained:

| Time, days | Epoxide, meq/g |
| --- | --- |
| 0 | 4.92 |
| 9 | 4.93 |
| 17 | 4.91 |
| 31 | 4.74 | d. Solution of 95.1% GTA hydrate (85% of anhydrous GTA and 15% water)

This solution initially had an epoxide content of 5.10 meq/g. After standing for 38 days at 20° C. the content was still 5.08 meq/g and after 57 days at 20° C. it was still 5.03 meq/g.

e. Solution of 90% GTA hydrate (80.5% anhydrous GTA and 19.5% water); influence of alkali In this case an accelerated aging experiment was carried out by keeping the mixture to be examined at 80° C. for 8 hours.

A first experiment was carried out without any additive. It appeared at 20° C. that a pH meter indicated a value of 12.2 in this concentrated solution. The epoxide content was 4.80 meq/g. After heating at 80° C. for 8 hours the content had decreased to 3.97 meq/g.

In a second experiment a small amount of NaOH was added initially until the pH meter at 20° C. indicated a value of 13.4. This time the epoxide decreased in 8 hours at 80° C. from 4.80 meq/g to zero.

3. Azeotropic distillation of epichlorohydrin from a solution of GTA hydrate a. 54.9 Grams of anhydrous GTA powder having a content of 3.6% of epichlorohydrin were dissolved in 55.7 grams of water. The epoxide content of this solution was 3.06 meq/g. The solution was subjected to distillation at 60° C. and at a pressure which initially was 2.67 kPa and during evaporation of the water gradually decreased to 1.06 kPa. After 15 minutes the epichlorohydrin content has decreased to 120 ppm. By continuing the distillation for a further 15 minutes the epichlorohydrin content decreased to 15 ppm. The product obtained after this distillation had an epoxide content of 5.48 meq/g and still contained 8.7% of water, which is less than the water content of the hydrate. Because the crystallization of the hydrate, as appears from the above-described preparation thereof, takes a relatively long time and low temperature, the mixture remained liquid. By addition of water a solution of 95% GTA hydrate was prepared.

b. 163.6 Grams of the same anhydrous GTA were dissolved in 70.0 grams of water. The obtained solution had an epoxide content of 4.29 meq/g. Water was distilled off at 40° C., wherein the pressure which initially was 2.67 kPa decreased gradually during the removal of the water to 1.06 kPa.

After 15 minutes the epichlorohydrin content was still 950 ppm; after a further 15 minutes the epichlorohydrin content had decreased to 190 ppm and after a further 30 minutes the epichlorohydrin content was still only 18 ppm. The epoxide content was 5.23 meq/g. By addition of water the concentration of GTA hydrate was adjusted to 92%.

c. 51.0 Grams of the same anhydrous GTA were dissolved in 51.6 grams of water. The epoxide content of this solution was 3.05 meq/g. Water was distilled from the solution under the same conditions as in experiment b. After 15 minutes the epichlorohydrin content was still 60 ppm. After a further 15 minutes the epichlorohydrin content was 1.5 ppm. Thereafter the distillation was continued during a further 30 minutes, whereby the epichlorohydrin content remained constant at 1.5 ppm. After this distillation the epoxide content was 5.28 meq/g (theoretical value also 5.28 meq/g) and the water content was 12%. By addition of water the GTA hydrate content was adjusted at 90%.

What is claimed is:

1. Stable concentrated aqueous solution of glycidyltrimethylammonium chloride, said solution containing the monohydrate of glycidyltrimethylammonium chloride in a concentration of 90% to saturation and after dilution with water to a content of 25% glycidyltrimethylammonium chloride shows a pH of less than 12.5.

2. The stable concentrated solution of claim 1, wherein said solution contains less than 70 ppm of epichlorohydrin, based on the anhydrous glycidyltrimethylammonium chloride.

3. A process for preparing a stable concentrated aqueous solution of glycidyltrimethylammonium chloride, comprising mixing anhydrous glycidyltrimethylammonium chloride with water to prepare an aqueous solution containing 20–70% glycidyltrimethylammonium chloride, and, by evaporation of water at a pressure of less than 15 kPa, concentrating this solution to a concentration corresponding to at least 90% of the monohydrate of glycidyltrimethylammonium chloride.

4. A process in accordance with claim 3 wherein said anhydrous glycidyltrimethylammonium chloride contains residual epichlorohydrin, whereby said epichlorohydron forms an azeotrope with the water and is removed by said evaporation step.

5. The monohydrate of glycidyltrimethylammonium chloride.

* * * * *